(12) United States Patent
Joshi et al.

(10) Patent No.: US 9,533,066 B2
(45) Date of Patent: Jan. 3, 2017

(54) VOLATILE SUBSTANCE DELIVERY SYSTEM

(71) Applicant: Microlin, LLC, Salt Lake City, UT (US)

(72) Inventors: Ashok V Joshi, Salt Lake City, UT (US); David J Erekson, Tooele, UT (US)

(73) Assignee: Microlin, LLC, Salt Lake City, UT (US)

( * ) Notice: Subject to any disclaimer, the term of this patent is extended or adjusted under 35 U.S.C. 154(b) by 128 days.

(21) Appl. No.: 14/632,970

(22) Filed: Feb. 26, 2015

(65) Prior Publication Data

US 2015/0238647 A1    Aug. 27, 2015

Related U.S. Application Data

(63) Continuation-in-part of application No. 14/537,691, filed on Nov. 10, 2014.

(60) Provisional application No. 61/944,698, filed on Feb. 26, 2014.

(51) Int. Cl.
*A61L 9/12* (2006.01)
*B01F 3/04* (2006.01)
*F04B 19/12* (2006.01)

(52) U.S. Cl.
CPC .. *A61L 9/12* (2013.01); *B01F 3/04* (2013.01); *F04B 19/12* (2013.01)

(58) Field of Classification Search
CPC ...................................... B01F 3/04; A61L 9/12
USPC ............ 261/72.1, 81, 82, DIG. 88; 239/326
See application file for complete search history.

(56) References Cited

U.S. PATENT DOCUMENTS

| | | | | |
|---|---|---|---|---|
| 2,179,871 A * | 11/1939 | Vogel | ........................ | B05B 9/08 239/326 |
| 2,348,420 A * | 5/1944 | Rose | ..................... | B05B 7/2491 239/326 |
| 4,623,337 A | 11/1986 | Maurice | | |
| 5,879,095 A | 3/1999 | Gueret | | |
| 8,566,972 B2 * | 10/2013 | Vogtner | ................. | A61H 33/60 222/372 |
| 2005/0036823 A1 | 2/2005 | Butcher et al. | | |
| 2005/0185940 A1 | 8/2005 | Joshi et al. | | |
| 2006/0292304 A1 | 12/2006 | Tisone | | |

OTHER PUBLICATIONS

Copenheaver et al. "International Search Report" for PCT Application No. PCT/US2015/017837, mailed Jun. 3, 2015, 2 pages.
Copenheaver et al. "Written Opinion of the International Searching Authority" for PCT Application No. PCT/US2015/017837, mailed Jun. 3, 2015, 8 pages.

\* cited by examiner

*Primary Examiner* — Robert A Hopkins
(74) *Attorney, Agent, or Firm* — Brian C. Trask

(57) ABSTRACT

A volatile substance delivery system includes a volatile substance container to contain a volatile substance, an outlet to deliver a volume of the volatile substance from the volatile substance container to an ambient environment, and a manual screw pump to increase pressure within the volatile substance container and promote the delivery of the volatile substance from the volatile substance container.

17 Claims, 8 Drawing Sheets

VOLATILE SUBSTANCE DELIVERY SYSTEM

CROSS-REFERENCE TO RELATED APPLICATIONS

This application claims the benefit of U.S. Provisional Application No. 61/944,698, filed on Feb. 26, 2014, which is incorporated by reference herein in its entirety. Also, this application is a continuation-in-part of U.S. application Ser. No. 14/537,691, filed on Nov. 10, 2014, which is incorporated by reference herein in its entirety.

BACKGROUND

Conventional fragrance delivery systems use wicking to transfer the fragrance from a reservoir to a point of release from the device. However, wicking systems are inherently subject to many environmental conditions. This impacts the ability of the fragrance delivery system to control the release of the fragrance into the ambient environment. Without the ability to control the release of the fragrance, top notes typically evaporate first, followed by middle notes and then base notes (based on different volatility levels). In this way, conventional wicking systems over time often fail to provide full fragrances with the full range of combined notes.

SUMMARY

Embodiments of a system are described. In one embodiment, the system is a volatile substance delivery system. An embodiment of the volatile substance delivery system includes a volatile substance container, and outlet, and a manual screw pump. The volatile substance container contains the volatile substance. The outlet delivers a volume of the volatile substance from the volatile substance container to an ambient environment. The manual screw pump increases pressure within the volatile substance container and promotes the delivery of the volatile substance from the volatile substance container. Other embodiments of the system are also described.

Embodiments of a method are also described. In one embodiment, the method for operating a volatile substance delivery system includes twisting a manual screw pump. The method also includes compressing fluid within a volatile substance container in response to twisting the manual screw pump. The volatile substance container contains a volatile substance. The method also includes delivering a volume of the volatile substance from and outlet of the volatile substance container to an ambient environment in response to compressing the fluid within the volatile substance container. Other embodiments of the method are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
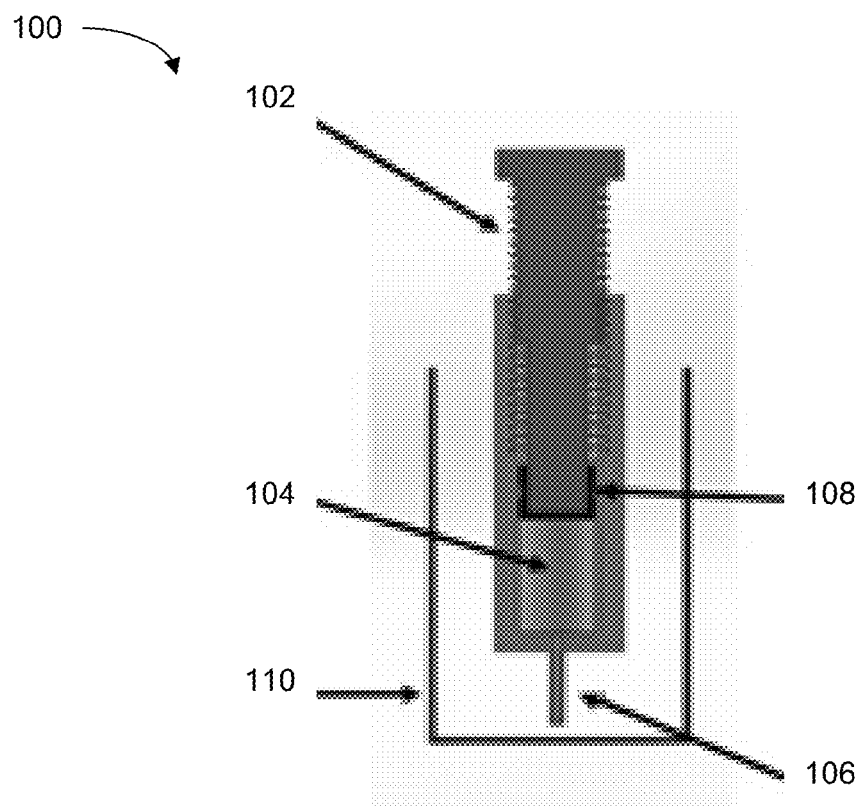
FIG. 1 illustrates one embodiment of a sealed manual fragrance delivery system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments facilitate on-demand delivery of a volatile substance. In general, the volatile substance refers to any fluid which is volatile such that it diffuses, evaporates, or otherwise changes in characteristics over time in certain environments. In some embodiments, the volatile substance may be a fragrance. Other embodiments may utilize other types of volatile substances. References to embodiments which utilize a fragrance are set forth as examples, but are not limiting to embodiments of the delivery system, which may deliver any of a variety of volatile substances.

The on-demand delivery of a fragrance or other volatile substance may be used to create an expected ambiance or environment for a user. For example, a user may utilize fragrance to optimize the user's sleeping environment and to enhance the user's bedtime routine. As another example, a user may utilize fragrance to enhance the user's vehicle environment and driving routine. Examples of other activities that may benefit from the use of fragrances include, but are not limited to, sleeping, studying, working, eating, and watching television.

In contrast to conventional wicking systems, embodiments described herein implement drop delivery systems. Drop delivery systems may be controlled more easily than conventional systems. Also, drop delivery systems can maintain a full or broader range of notes over a longer period of time, if the fragrance is not subjected to evaporation or other degrading environmental conditions. This allows each drop of the fragrance to deliver a mix of top, middle, and base notes throughout the operating lifecycle of a fragrance volume within a fragrance delivery system.

Embodiments of a volatile substance delivery system incorporate a volatile substance container to contain the volatile substance. The system also includes an outlet to deliver a volume of the volatile substance from the volatile substance container to an ambient environment. The outlet may be directly from the volatile substance container or, in other embodiments, from a downstream container or channel. The system also includes a manual screw pump to increase pressure within the volatile substance container and promote the delivery of the volatile substance from the volatile substance container. In further embodiments, the delivery system may include a combination of one or more additional components such as an emanator, a fan, a heat source for heating air, a heat source for heating the fragrance, and so forth. Other embodiments may include additional components.

A primary advantage of some embodiments described herein includes the ability to deliver the full depth of the fragrance, as opposed to just the high notes. In some embodiments, the system provides an immediate volume of fragrance that is then distributed into the ambient environment, to optimize an environment for a given activity. The volume of fragrance delivered is not subject to environmental conditions.

FIG. 1 illustrates one embodiment of a sealed manual fragrance delivery system 100. The illustrated fragrance delivery system 100 includes a manual screw pump 102, a fragrance container 104, an outlet 106, a piston plunger 108, and an emanator 110. Although the illustrated fragrance delivery system 100 includes certain components to achieve specific functionality, other embodiments of the pressurized chamber fragrance delivery system 100 may include fewer or more components to achieve similar or different functionality.

In one embodiment, the manual screw pump 102 is used to pressurize the fragrance container 104 containing the fragrance or other volatile substance. Any type of manual screw pump may be implemented. In some embodiments, the manual screw pump may have an exposed surface for engagement by a user's hand to manually turn the screw pump. In other embodiments, the manual screw pump may have a mechanical tool engagement surface for engagement of a mechanical tool such as a screwdriver or other hand tool to manually turn the screw pump.

In further embodiments, the manual screw pump may have either infinite or discrete turning positions. Infinite turning positions refer to the ability to rotate the manual screw pump 102 to any angle, without limitation to specific angles. In contrast, discrete turning positions refer to rotational steps, or increments, at which the manual screw pump 102 engages. For example, an embodiment of the manual screw pump 102 may have a fixed number of rotational positions (e.g., 2, 3, 5, 8, 10, 12, etc.) to which the piston plunger 108 will rotate within a single full rotation of the manual screw pump 102. Due to the helical arrangement of the screw threads, each fixed position corresponds to a unique fixed translational position of the piston plunger 108 relative to the outlet 106. Similarly, each fixed position also corresponds to a unique fixed volume of the fragrance container 104, and fixed incremental changes in that volume.

The piston plunger 108 is sealed to separate the threaded sidewalls from the portion of the fragrance container 104 that contains the fragrance or other volatile substance. The piston plunger 108 also seals the fragrance portion of the fragrance container 104 so that it can be pressurized, at least temporarily.

Pressurizing the fragrance container 104 causes the fragrance to be expelled from the fragrance container 104 through the outlet 106 to the emanator 110. The outlet may or may not include a valve or other control mechanism to control when the pressurized fragrance is released from the fragrance container 104. Once released and delivered to the emanator 110, the fragrance can evaporate into the ambient environment from the emanator 110. In further embodiments, additional mechanical and/or thermal assistance may be provided to accelerate evaporation of the fragrance from the emanator 110.

Some examples of emanator materials include, but are not limited to, porous polymers, simple cellular papers or films. In general, embodiments of the emanator 110 have a balance of absorption, wicking, and emanation properties that allow the emanator 110 to collect, distribute, and release the fragrance over time. In the illustrated embodiment, the emanator 110 at least partially or fully wraps around the fragrance container 104.

In some embodiments, the emanator 112 includes a porous material to collect, wick, and release the fragrance. The emanator 112 may or may not have its own structural integrity to maintain a specific shape while mounted within the fragrance delivery system. In some embodiments, the emanator material is applied to, or supported by, another support structure such as a cage or frame made of any suitable material.

Figure 2:
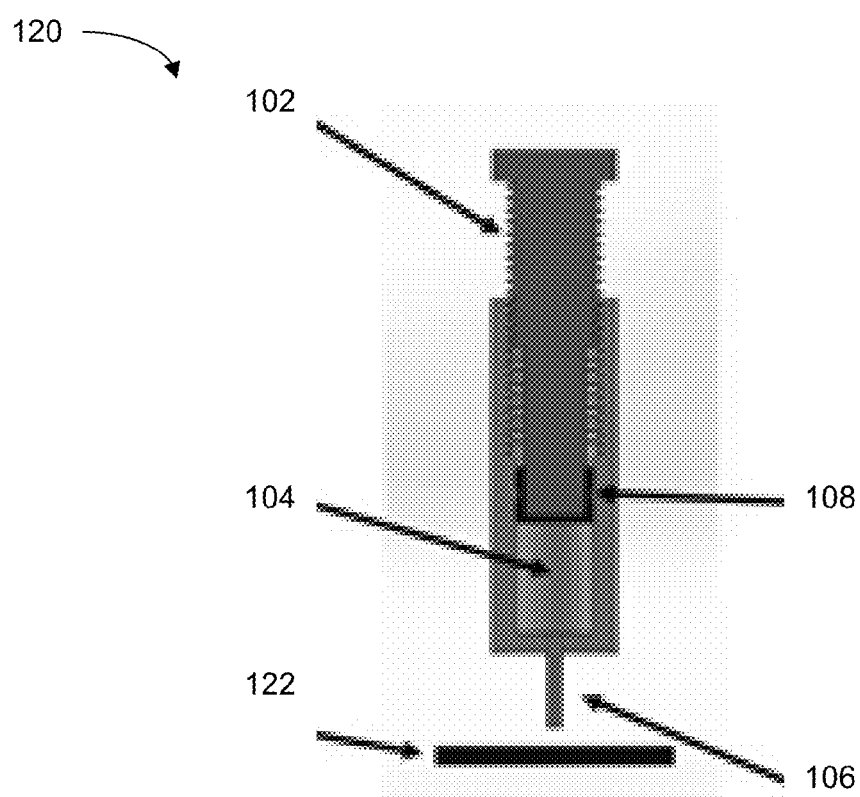
FIG. 2 illustrates another embodiment of a sealed manual fragrance delivery system which includes a separate emanator.

FIG. 2 illustrates another embodiment of a sealed manual fragrance delivery system 120 which includes a separate emanator 122. In contrast to the emanator 110 of FIG. 1, the emanator 122 of FIG. 2 is separated from the rest of the delivery system assembly. In other words, the emanator 122 does not wrap around parts of the fragrance container 104, and there is a distance of separation between the outlet 106 and the nearest surface of the emanator 122. In these embodiments, the delivery system 120 may be oriented to facilitate dropping the emitted fragrance from the outlet 106 to the emanator 122.

In other embodiments, the outlet 106 includes a valve or other control mechanism to control how much of the pressurized fragrance is released from the fragrance container 104 at a single time. The valve or other control mechanism may allow pressure to build up within the fragrance container 102 until a threshold pressure has been reached, at which point the valve or other control mechanism may release a fixed volume of the fragrance is released. Alternatively, the valve or other control mechanism may release a variable volume of the fragrance until the pressure within the fragrance container 102 falls below a lower threshold pressure. In either case, the pressure of the fragrance may facilitate projecting or spraying the fragrance onto the emanator. In some embodiments, this pressurized transfer of the fragrance may facilitate a variety of orientations of the delivery system 102, instead of relying solely on gravity fed transfer.

Figure 3:
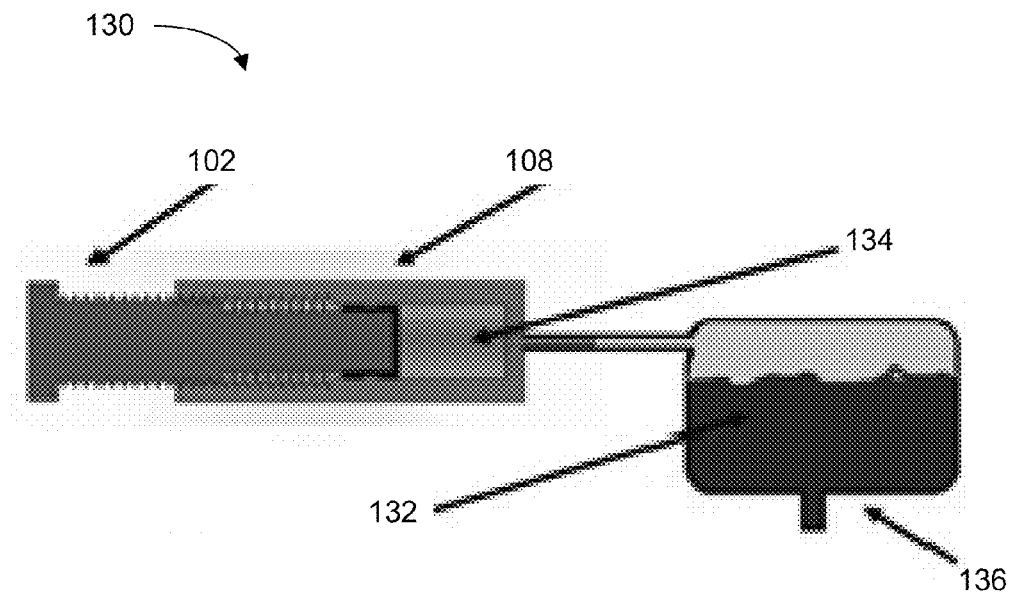
FIG. 3 illustrates another embodiment of a sealed manual fragrance delivery system which includes a separate fragrance chamber.

FIG. 3 illustrates another embodiment of a sealed manual fragrance delivery system 130 which includes a separate fragrance container 132. The piston plunger 108 is used to pressurize an intermediate container 134 of inert gas or liquid, which transfers through a channel to the separate fragrance container 132. As the pressure in the intermediate container 134 is transferred to the separate fragrance container 132, the fragrance is emitted from the fragrance container 132 to an emanator (not shown) or directly into the ambient environment. If an emanator is used, the emanator may be wrapped around part of all of the separate fragrance container 132, or located remotely from the separate fragrance container 132.

In some embodiments, the delivery system 130 may include a valve or other control mechanism within the transfer channel between the intermediate container 134 and the separate fragrance container 132. The valve or other control mechanism may control the timing and/or volume and/or pressure of the transfer from the intermediate container 134 to the separate fragrance container 132.

Figure 4:
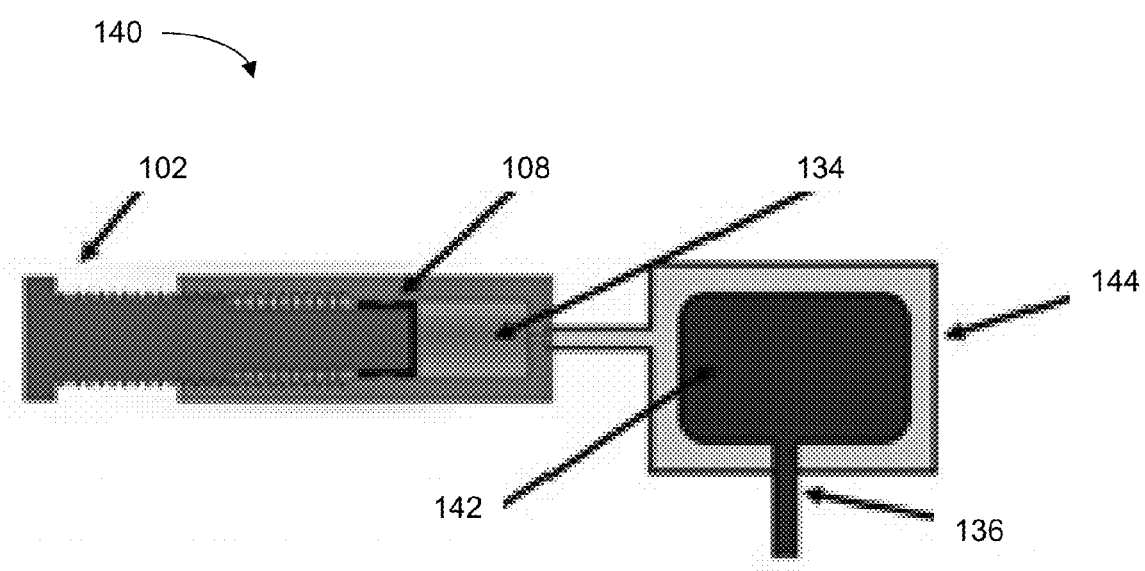
FIG. 4 illustrates another embodiment of a sealed manual fragrance delivery system which includes a separate flexible fragrance chamber.

FIG. 4 illustrates another embodiment of a sealed manual fragrance delivery system 140 which includes a separate flexible fragrance container 142. The separate flexible fragrance container 142 is disposed within a rigid outer housing 144. The piston plunger 108 is used to pressurize the intermediate container 134 of inert gas or liquid, which transfers through the channel to the outer housing 144. As the pressure in the outer housing 144 increases, the separate flexible fragrance container 142 is compressed and the fragrance is emitted to an emanator (not shown) or directly into the ambient environment.

Figure 5:
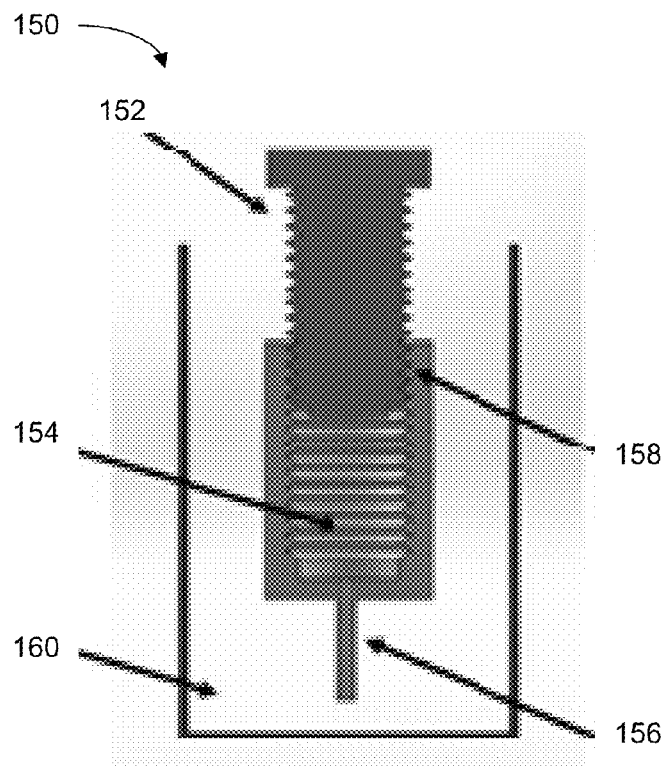
FIG. 5 illustrates another embodiment of a sealed manual fragrance delivery system which includes a manual screw pump with sealed threads.

FIG. 5 illustrates another embodiment of a sealed manual fragrance delivery system 150 which includes a manual screw pump 152 with sealed threads 158. The illustrated fragrance delivery system 150 includes the manual screw pump 152, a fragrance container 154, an outlet 156, the sealed threads 158, and an emanator 160. Although the illustrated fragrance delivery system 150 includes certain components to achieve specific functionality, other embodiments of the pressurized chamber fragrance delivery system 150 may include fewer or more components to achieve similar or different functionality.

The delivery system 150 of FIG. 5 is similar in many aspects to the delivery system 100 of FIG. 1, with the exception of the sealed threads 158 of FIG. 5. In the delivery system 100 of FIG. 1, the use of the sealed piston plunger 108 made it unnecessary to use sealed threads. However in the delivery system 150 of FIG. 5, the sealed threads 158. This alleviates the need for a separate seal.

As the threaded wall of the screw engages the corresponding threads on the interior sidewall of the fragrance container 154, the pressure within the fragrance container 154 increase and forces the fragrance to pass through the outlet 156 onto the emanator 160.

Figure 6:
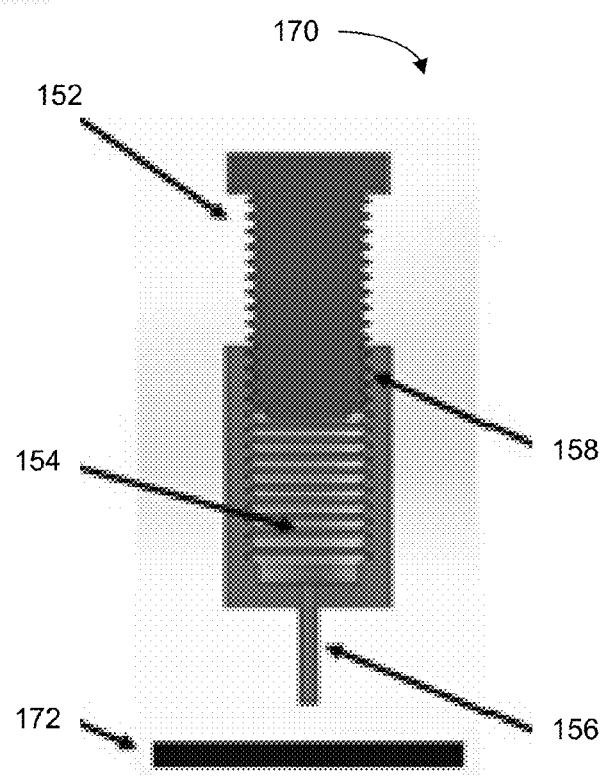
FIG. 6 illustrates another embodiment of a sealed manual fragrance delivery system which includes a separate emanator.

FIG. 6 illustrates another embodiment of a sealed manual fragrance delivery system 170 which includes a separate emanator 172. In contrast to the emanator 160 of FIG. 5, the emanator 172 of FIG. 6 is separated from the rest of the delivery system assembly, similar to the separate emanator 122 of FIG. 2.

Figure 7:
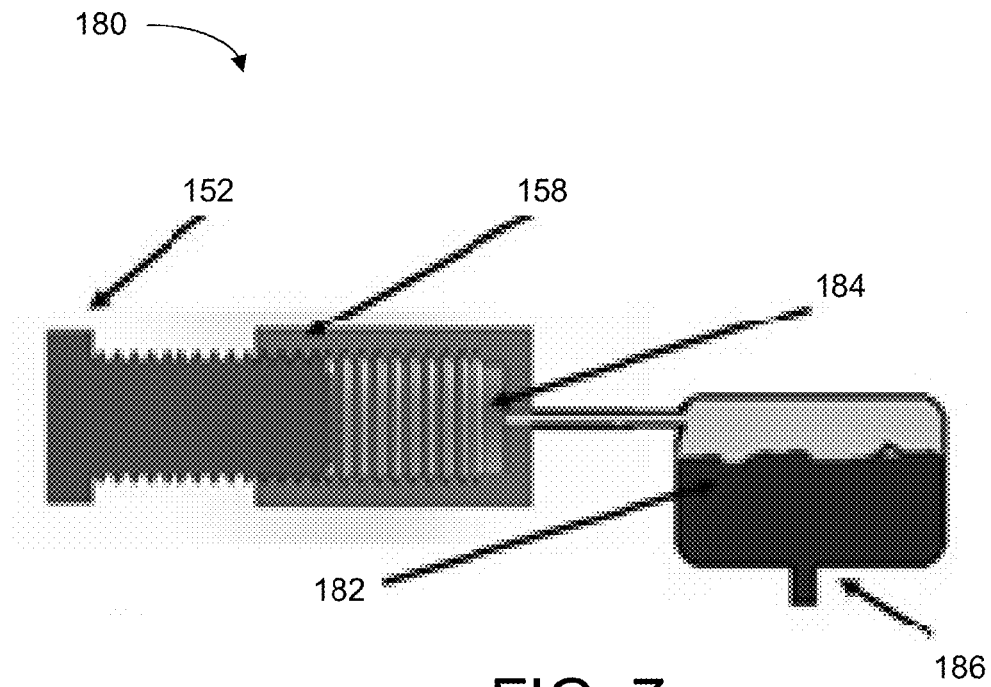
FIG. 7 illustrates another embodiment of a sealed manual fragrance delivery system which includes a manual screw pump with sealed threads and a separate fragrance chamber.

FIG. 7 illustrates another embodiment of a sealed manual fragrance delivery system 180 which includes a manual screw pump 152 with sealed threads 158 and a separate fragrance container 182. The manual screw pump 152 is used to pressurize an intermediate container 184 of inert gas or liquid, which transfers through a channel to the separate fragrance container 182. As the pressure in the intermediate container 184 is transferred to the separate fragrance container 182, the fragrance is emitted from the fragrance container 182 to an emanator (not shown) or directly into the ambient environment. If an emanator is used, the emanator may be wrapped around part of all of the separate fragrance container 182, or located remotely from the separate fragrance container 182.

Figure 8:
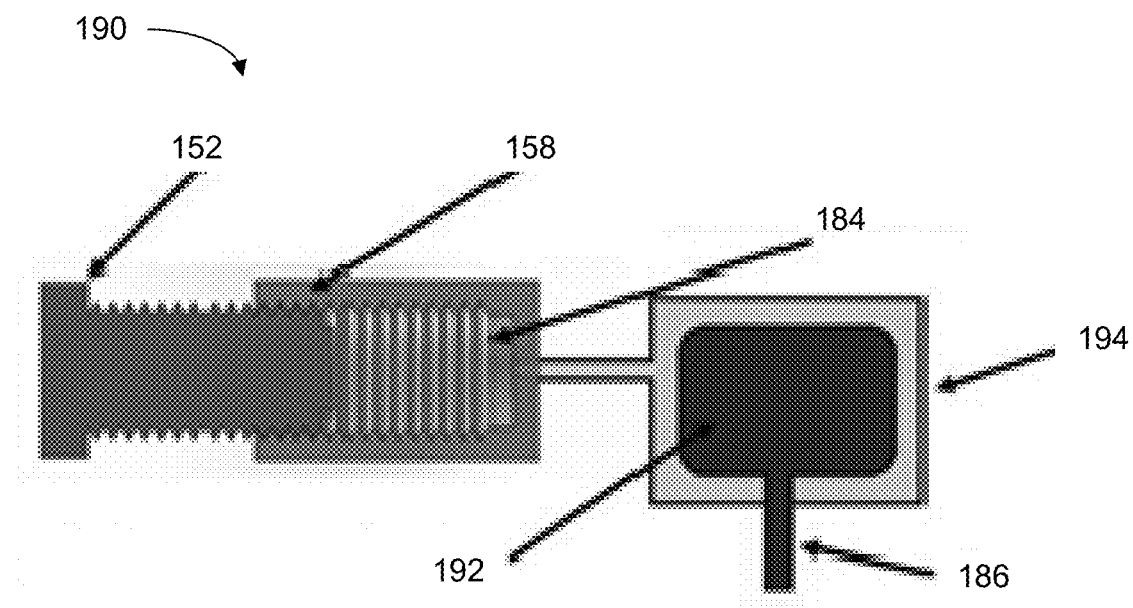
FIG. 8 illustrates another embodiment of a sealed manual fragrance delivery system which includes a manual screw pump with sealed threads and a separate flexible fragrance chamber.

FIG. 8 illustrates another embodiment of a sealed manual fragrance delivery system 190 which includes a manual screw pump 152 with sealed threads 158 and a separate flexible fragrance container 192. The separate flexible fragrance container 192 is disposed within a rigid outer housing 194. The manual screw pump 152 is used to pressurize the intermediate container 184 of inert gas or liquid, which transfers through the channel to the outer housing 194. As the pressure in the outer housing 194 increases, the separate flexible fragrance container 192 is compressed and the fragrance is emitted to an emanator (not shown) or directly into the ambient environment.

Figure 9:
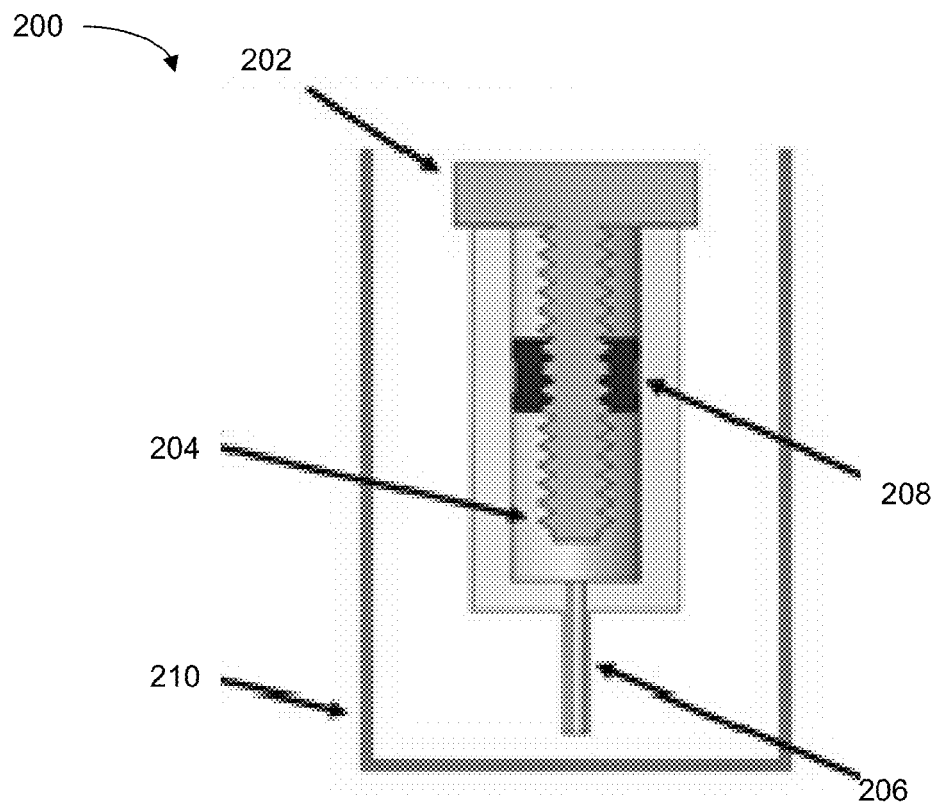
FIG. 9 illustrates another embodiment of a sealed manual fragrance delivery system which includes a sealed piston and a separate emanator.

FIG. 9 illustrates another embodiment of a sealed manual fragrance delivery system 200 which includes a sealed piston 208 and an emanator 210 enclosing the assembly. The illustrated fragrance delivery system 200 includes a manual screw pump 202, a fragrance container 204, an outlet 206, the sealed piston 208, and the emanator 210. Although the illustrated fragrance delivery system 200 includes certain components to achieve specific functionality, other embodiments of the pressurized chamber fragrance delivery system 200 may include fewer or more components to achieve similar or different functionality.

The delivery system 200 of FIG. 9 is similar in many aspects to the delivery system 100 of FIG. 1, with the exception of the location of the sealed piston plunger 208. In the delivery system 100 of FIG. 1, the sealed piston plunger 108 is located at an end of the threaded screw, which moves as a whole toward the outlet 106. In contrast, the threaded screw of FIG. 9 rotates, but does not move toward or away from the outlet 206. The sealed piston plunger 208 moves along the threaded screw as it is rotated, decreasing the volume between the sealed piston plunger 108 and the outlet 206. This alleviates the need for additional clearance at the head of the manual screw pump 202.

Figure 10:
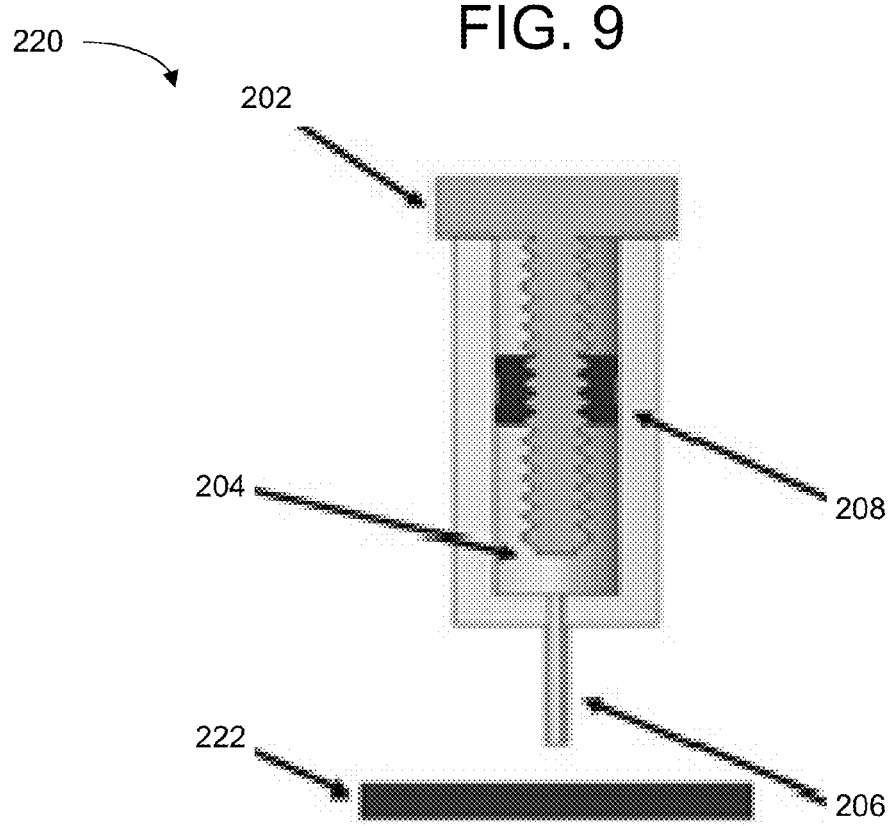
FIG. 10 illustrates another embodiment of a sealed manual fragrance delivery system which includes a sealed piston and an emanator enclosing the assembly.

FIG. 10 illustrates another embodiment of a sealed manual fragrance delivery system 220 which includes a sealed piston 208 and a separate emanator 222. In contrast to the emanator 210 of FIG. 9, the emanator 222 of FIG. 10 is separated from the rest of the delivery system assembly, similar to the separate emanator 122 of FIG. 2.

Figure 11:
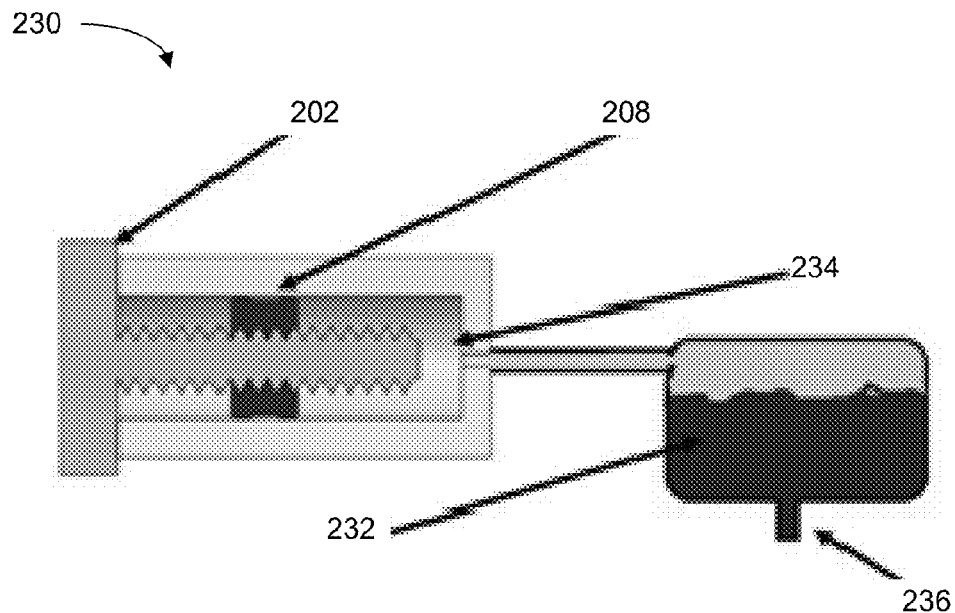
FIG. 11 illustrates another embodiment of a sealed manual fragrance delivery system which includes a sealed piston and a separate fragrance chamber.

FIG. 11 illustrates another embodiment of a sealed manual fragrance delivery system 230 which includes a sealed piston 208 and a separate fragrance container 232. The manual screw pump 202 is used to pressurize an intermediate container 234 of inert gas or liquid, which transfers through a channel to the separate fragrance container 232. As the pressure in the intermediate container 234 is transferred to the separate fragrance container 232, the fragrance is emitted from the fragrance container 232 to an emanator (not shown) or directly into the ambient environment. If an emanator is used, the emanator may be wrapped around part of all of the separate fragrance container 232, or located remotely from the separate fragrance container 232.

Figure 12:
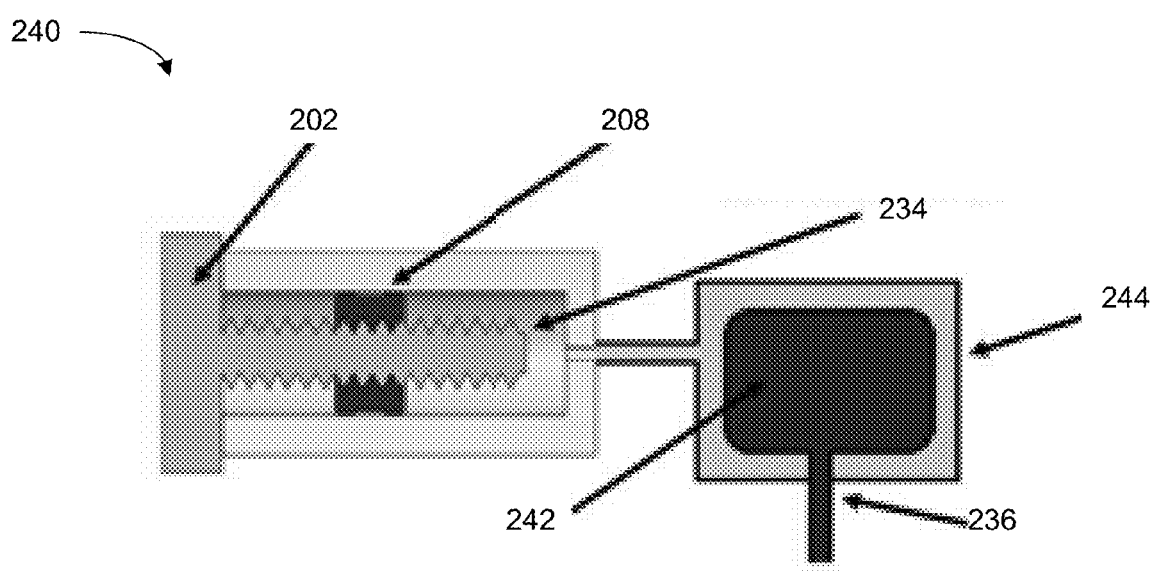
FIG. 12 illustrates another embodiment of a sealed manual fragrance delivery system which includes a sealed piston and a separate flexible fragrance chamber.

FIG. 12 illustrates another embodiment of a sealed manual fragrance delivery system 240 which includes a sealed piston 208 and a separate flexible fragrance container 242. The separate flexible fragrance container 242 is disposed within a rigid outer housing 244. The manual screw pump 202 is used to pressurize the intermediate container 234 of inert gas or liquid, which transfers through the channel to the outer housing 244. As the pressure in the outer housing 244 increases, the separate flexible fragrance container 242 is compressed and the fragrance is emitted to an emanator (not shown) or directly into the ambient environment.

Figure 13:
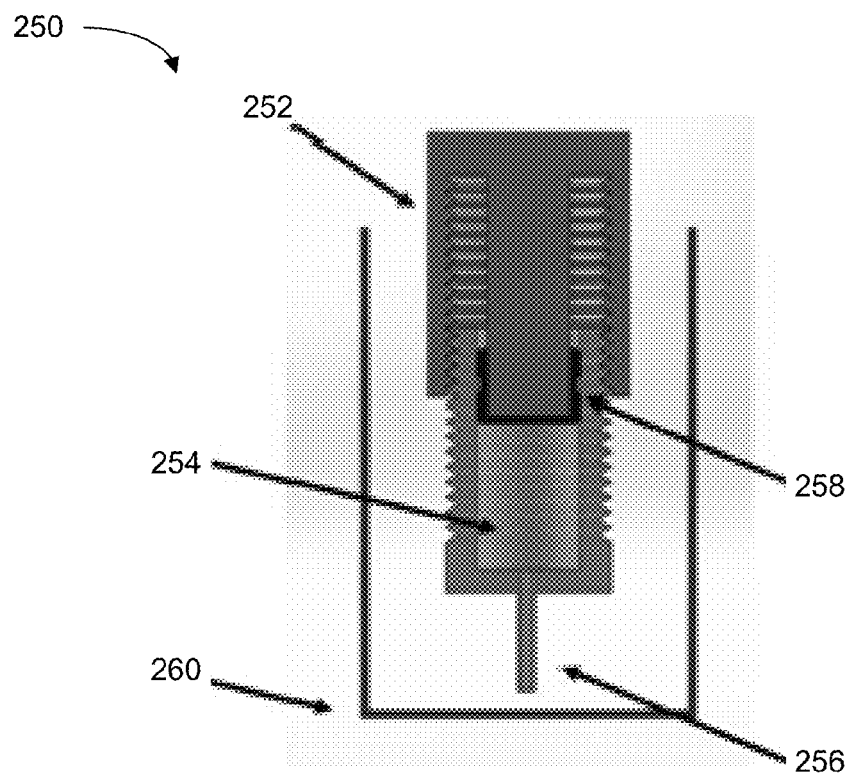
FIG. 13 illustrates another embodiment of a sealed manual fragrance delivery system which includes external threads outside of a piston chamber.

FIG. 13 illustrates another embodiment of a sealed manual fragrance delivery system 250 which includes external threads outside of a fragrance container 254. The illustrated fragrance delivery system 250 includes a manual screw pump 252, a fragrance container 254, an outlet 256, a sealed piston 258, and an emanator 260. Although the illustrated fragrance delivery system 250 includes certain components to achieve specific functionality, other embodiments of the pressurized chamber fragrance delivery system 250 may include fewer or more components to achieve similar or different functionality.

The delivery system 250 of FIG. 9 is similar in many aspects to the delivery system 100 of FIG. 1, with the exception of the location of the threads for the manual screw pump 252. In the delivery system 100 of FIG. 1, the threads are located inside the same cavity as the fragrance container 104. Specifically, the threads are located on the outside wall of the central post, and corresponding threads are located on the inner sidewall of the cavity as the fragrance container 104. In contrast, the threads for the embodiment of FIG. 13 are located outside the cavity that contains the fragrance. Instead, the threads are located on wall surfaces other than on the post. This may allow the piston plunger 258 to seal between two smooth walls.

Figure 14:
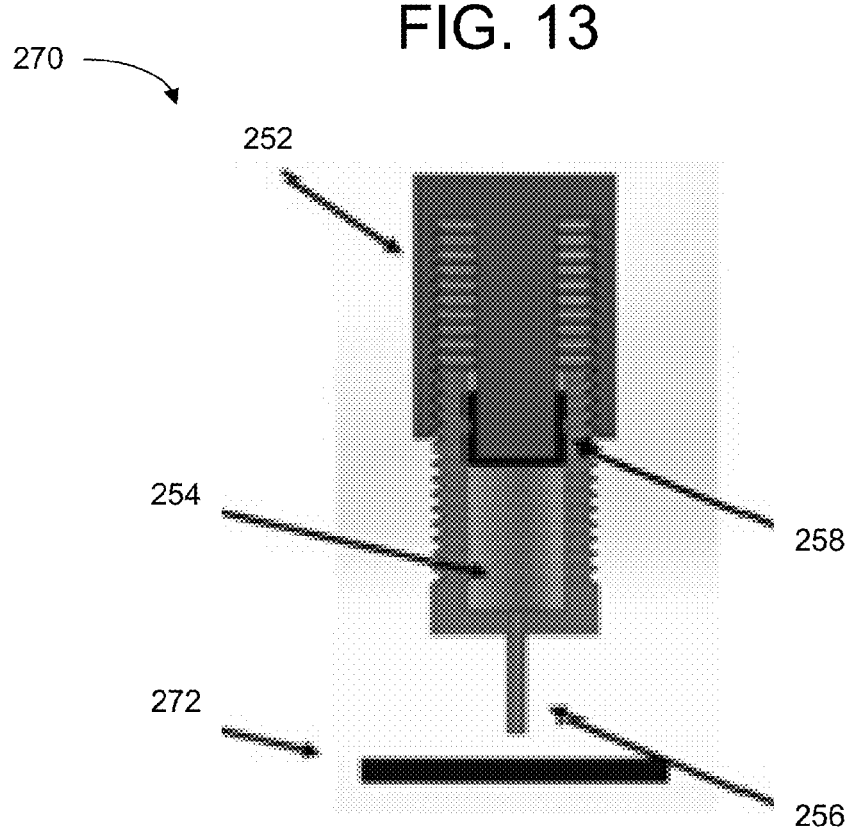
FIG. 14 illustrates another embodiment of a sealed manual fragrance delivery system which includes external threads outside of a piston chamber and a separate emanator.

FIG. 14 illustrates another embodiment of a sealed manual fragrance delivery system 170 which includes external threads outside of a fragrance container 254 and a separate emanator 272. In contrast to the emanator 260 of FIG. 13, the emanator 272 of FIG. 14 is separated from the rest of the delivery system assembly, similar to the separate emanator 122 of FIG. 2.

Figure 15:
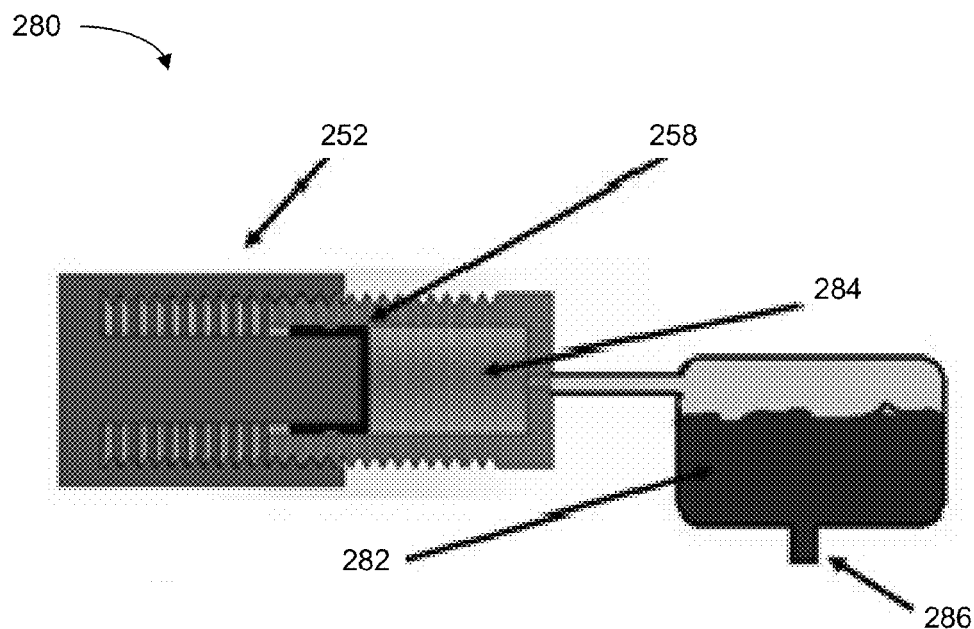
FIG. 15 illustrates another embodiment of a sealed manual fragrance delivery system which includes external threads outside of a piston chamber and a separate fragrance chamber.

FIG. 15 illustrates another embodiment of a sealed manual fragrance delivery system 280 which includes external threads and a separate fragrance container 282. The manual screw pump 252 is used to pressurize an intermediate container 284 of inert gas or liquid, which transfers through a channel to the separate fragrance container 282. As the pressure in the intermediate container 284 is transferred to the separate fragrance container 282, the fragrance is emitted from the fragrance container 282 to an emanator (not shown) or directly into the ambient environment. If an emanator is used, the emanator may be wrapped around part of all of the separate fragrance container 282, or located remotely from the separate fragrance container 282.

Figure 16:
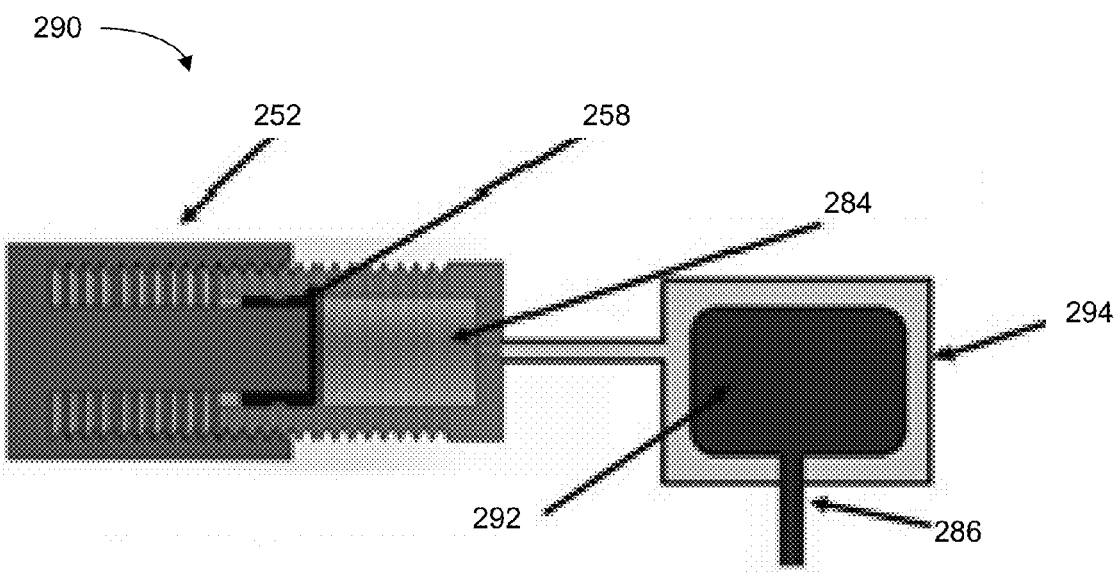
FIG. 16 illustrates another embodiment of a sealed manual fragrance delivery system which includes external threads outside of a piston chamber and a separate flexible fragrance chamber.

FIG. 16 illustrates another embodiment of a sealed manual fragrance delivery system 290 which includes external threads and a separate flexible fragrance container 292. The separate flexible fragrance container 292 is disposed within a rigid outer housing 294. The manual screw pump 252 is used to pressurize the intermediate container 284 of inert gas or liquid, which transfers through the channel to the outer housing 294. As the pressure in the outer housing 294 increases, the separate flexible fragrance container 292 is compressed and the fragrance is emitted to an emanator (not shown) or directly into the ambient environment.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A volatile substance delivery system comprising:
    a volatile substance container to contain a volatile substance;
    an outlet to deliver a volume of the volatile substance from the volatile substance container to an ambient environment; and
    a manual screw pump to increase pressure within the volatile substance container and promote the delivery of the volatile substance from the volatile substance container, wherein the manual screw pump comprises a threaded wall and a piston plunger, wherein the piston plunger engages a non-threaded sidewall of a plunger chamber, wherein the plunger chamber is coupled to a volatile substance housing by a fluid channel to transfer fluid from the plunger chamber to the volatile substance housing, wherein the volatile substance housing has a fixed volume, and the volatile substance container comprises a flexible container configured to compress and release the volatile substance in response to a transfer of fluid from the plunger chamber to the volatile substance housing.

2. The volatile substance delivery system of claim 1, wherein the threaded wall engages a threaded inner sidewall of the volatile substance container, and the piston plunger engages a non-threaded sidewall of the volatile substance container to create a seal between the piston plunger and the non-threaded sidewall of the volatile substance container.

3. The volatile substance delivery system of claim 1, wherein the piston plunger engages a non-threaded sidewall of a plunger chamber, wherein the plunger chamber is coupled to the volatile substance container by a fluid channel to transfer fluid from the plunger chamber to the volatile substance container.

4. The volatile substance delivery system of claim 1, wherein the manual screw pump comprises a threaded wall to engage a threaded inner sidewall of the volatile substance container.

5. The volatile substance delivery system of claim 4, wherein the threaded wall engages the threaded inner sidewall of the volatile substance container to create a seal between the threaded wall and the threaded inner sidewall.

6. The volatile substance delivery system of claim 1, wherein the manual screw pump comprises a threaded wall to engage a threaded inner sidewall of a plunger chamber, wherein the plunger chamber is coupled to the volatile substance container by a fluid channel to transfer fluid from the plunger chamber to the volatile substance container.

7. The volatile substance delivery system of claim 1, wherein the manual screw pump comprises a threaded wall and a piston plunger, wherein the threaded wall engages a threaded inner sidewall of the piston plunger to move the piston plunger in response to rotation of the threaded wall.

8. The volatile substance delivery system of claim 7, wherein an outer wall of the piston plunger engages a non-threaded sidewall of the volatile substance container to create a seal between the piston plunger and the non-threaded sidewall of the volatile substance container.

9. The volatile substance delivery system of claim 7, wherein an outer wall of the piston plunger engages a non-threaded sidewall of a plunger chamber, wherein the plunger chamber is coupled to the volatile substance container by a fluid channel to transfer fluid from the plunger chamber to the volatile substance container.

10. The volatile substance delivery system of claim 1, wherein the manual screw pump comprises a threaded wall, a central plunger post, and a plunger piston.

11. The volatile substance delivery system of claim 10, wherein the threaded wall engages a threaded outer sidewall of the volatile substance container, and the piston plunger engages a non-threaded inner sidewall of the volatile substance container to create a seal between the piston plunger and the non-threaded inner sidewall of the volatile substance container.

12. The volatile substance delivery system of claim 10, wherein the threaded wall engages the threaded outer sidewall of a plunger chamber, wherein the plunger chamber is coupled to the volatile substance container by a fluid channel to transfer fluid from the plunger chamber to the volatile substance container.

13. The volatile substance delivery system of claim 1, further comprising an emanator material aligned with the outlet, wherein the emanator material at least partially encompasses the volatile substance container.

14. The volatile substance delivery system of claim 1, further comprising an emanator material aligned with the outlet, wherein the emanator material is configured to receive the volume of the volatile substance through a transfer of the volatile substance from the outlet to the emanator material.

15. A volatile substance delivery system comprising:
    a volatile substance container to contain a volatile substance;
    an outlet to deliver a volume of the volatile substance from the volatile substance container to an ambient environment; and
    a manual screw pump to increase pressure within the volatile substance container and promote the delivery of the volatile substance from the volatile substance container; wherein
    the manual screw pump comprises a threaded wall to engage a threaded inner sidewall of a plunger chamber, wherein the plunger chamber is coupled to a volatile substance housing by a fluid channel to transfer fluid from the plunger chamber to the volatile substance housing, wherein the volatile substance housing has a fixed volume, and the volatile substance container comprises a flexible container configured to compress and release the volatile substance in response to a transfer of fluid from the plunger chamber to the volatile substance housing.

16. A volatile substance delivery system comprising:
    a volatile substance container to contain a volatile substance;
    an outlet to deliver a volume of the volatile substance from the volatile substance container to an ambient environment; and
    a manual screw pump to increase pressure within the volatile substance container and promote the delivery of the volatile substance from the volatile substance container,
    wherein the manual screw pump comprises a threaded wall and a piston plunger, wherein the threaded wall engages a threaded inner sidewall of the piston plunger to move the piston plunger in response to rotation of the threaded wall,
    wherein an outer wall of the piston plunger engages a non-threaded sidewall of a plunger chamber, wherein the plunger chamber is coupled to a volatile substance housing by a fluid channel to transfer fluid from the plunger chamber to the volatile substance housing, wherein the volatile substance housing has a fixed volume, and the volatile substance container comprises a flexible container configured to compress and release the volatile substance in response to a transfer of fluid from the plunger chamber to the volatile substance housing.

17. A volatile substance delivery system comprising:
a volatile substance container to contain a volatile substance;
an outlet to deliver a volume of the volatile substance from the volatile substance container to an ambient environment; and
a manual screw pump to increase pressure within the volatile substance container and promote the delivery of the volatile substance from the volatile substance container, wherein the manual screw pump comprises a threaded wall, a central plunger post, and a plunger piston, and
wherein the threaded wall engages the threaded outer sidewall of a plunger chamber, wherein the plunger chamber is coupled to a volatile substance housing by a fluid channel to transfer fluid from the plunger chamber to the volatile substance housing, wherein the volatile substance housing has a fixed volume, and the volatile substance container comprises a flexible container configured to compress and release the volatile substance in response to a transfer of fluid from the plunger chamber to the volatile substance housing.

* * * * *